United States Patent [19]

Overmyer

[11] Patent Number: 5,318,443
[45] Date of Patent: Jun. 7, 1994

[54] METHOD OF FLUSHING, DISINFECTING AND LUBRICATING A DENTAL TURBINE HANDPIECE

[76] Inventor: Thad J. Overmyer, 132 N. Second St., Danville, Ky. 40422

[21] Appl. No.: 79,410

[22] Filed: Jun. 21, 1993

Related U.S. Application Data

[63] Continuation-in-part of Ser. No. 968,344, Oct. 29, 1992.

[51] Int. Cl.⁵ ............................................. A61C 1/02
[52] U.S. Cl. ............................................. 433/104
[58] Field of Search .................... 433/104, 80, 101; 184/55.2

[56] References Cited

U.S. PATENT DOCUMENTS

| | | | |
|---|---|---|---|
| 3,556,669 | 1/1971 | Valeska et al. | 433/104 X |
| 3,963,391 | 6/1976 | Thorburn et al. | 433/104 X |
| 4,218,216 | 8/1980 | Sugai et al. | 433/104 X |
| 4,668,190 | 5/1987 | Overmyer | 433/80 |
| 4,695,255 | 9/1987 | Overmyer | 433/215 |
| 4,990,087 | 2/1991 | De Rocchis et al. | 433/104 |
| 5,054,584 | 10/1991 | Hoffman | 433/104 X |
| 5,131,845 | 7/1992 | Feldman et al. | 433/104 |

Primary Examiner—Gene Mancene
Assistant Examiner—Nicholas D. Lucchesi
Attorney, Agent, or Firm—Charles J. Brown

[57] ABSTRACT

A method of flushing, disinfecting and lubricating a dental turbine handpiece by forcing a pressurized solution of a disinfectant and lubricant simultaneously through an air drive line to the handpiece when it is not in operation to flush dental debris through an exhaust line.

16 Claims, 2 Drawing Sheets

METHOD OF FLUSHING, DISINFECTING AND LUBRICATING A DENTAL TURBINE HANDPIECE

CROSS REFERENCE TO RELATED APPLICATION

This application is a continuation-in-part of my co-pending application entitled "Method of Flushing, Disinfecting And Lubricating A Dental Turbine Handpiece" filed Oct. 29, 1992 and given Ser. No. 07/968,344.

BACKGROUND OF THE INVENTION

Dental instruments commonly include an air turbine driven by compressed air from a drive line. Such instruments include high and low speed turbine handpieces and scaling instruments, and all forms are referred to herein as turbine handpieces. The air drive line is routed within a flexible hose having an end fitting for removable attachment of the turbine handpiece. Also contained within the flexible hose are an exhaust line for returning the drive air after it has served its function in driving the turbine, a coolant line for removing excess heat from the dental work site, and in the case of high speed turbine handpieces a chip air line which mixes the compressed air with the coolant to generate a spray. During operation of dental turbine handpieces some debris from the mouth such as saliva, cuttings, coolant and pathogens, enters the turbine of the handpiece. The pressurized air that drives the turbine is not capable of flushing out this debris and indeed the debris may not even be fully flushed out during sterilization by autoclaving which normally is carried out on the handpiece after each use on a patient.

Dental turbine handpieces also require periodic lubrication. For this purpose the conventional practice is to remove the handpiece from the hose end fitting and connect it to an aerosol container of a lubricant which is typically of a petroleum base such as naphtha. A few bursts from the container serve to lubricate the moving parts of the turbine. The efficiency of the aerosol container decreases of course as its propellant is exhausted and it is by no means ideal that petroleum-based lubricant later enters the mouth of the patient, but those disadvantages have been tolerated.

It is the principal purpose of the present invention to provide a method by which the turbine of a dental handpiece may be disinfected after each use and flushed of all dental debris and simultaneously lubricated without necessitating the use of separate lubricant containers. This is to be achieved by forcing a pressurized solution of a disinfectant-lubricant through the air drive line to the turbine of the handpiece when it is not in operation on a patient, thus flushing dental debris through the exhaust line and effectively lubricating the moving parts of the turbine. Petroleum based lubricants are to be avoided.

My U.S. Pat. No. 4,668,190 describes apparatus for injecting a liquid solution into a dental water-injection system and certain of the components of that apparatus are useful in practicing the method of the present invention. I also describe in my U.S. Pat. No. 4,695,255 a method of lubricating human hard tissue during cutting by directing against that hard tissue a flow of solution which includes glycerin as a lubricating agent, and glycerin is the preferred lubricant in the practice of the present invention. Neither of these prior art references discloses any method of disinfecting and lubricating a dental turbine handpiece.

Elsewhere in the prior art it is known to deliver a liquid solution to a dental handpiece. For example U.S. Pat. No. 3,987,550 teaches the introduction of a prophylaxis material (a cleaning agent) through a slow speed handpiece and U.S. Pat. Nos. 3,949,753, 4,193,196 and 5,044,952 disclose other similar methods and apparatus. In each of them a solution is transmitted one way or the other through a dental instrument into the patient's mouth. None of those references, however, teaches the introduction of any solution through an air drive line of a dental turbine handpiece when it is not in operation, nor do they teach simultaneous disinfecting and lubricating of the turbine by the solution introduced through the air drive line.

U.S. Pat. No. 4,990,087 is also relevant because it discloses a method of lubricating, disinfecting and flushing a dental handpiece. However three distinct fluids are employed in that method. First a liquid lubricant from one bottle is passed through the air drive line to the turbine, then a liquid disinfectant from another bottle is passed through the coolant line but not the turbine air drive line and finally compressed air is injected for flushing. The method is deficient in that the disinfectant does not reach contaminating debris within the turbine or the chip air line. Moreover this method concludes with an air purging step which removes both excess disinfectant and lubricant. If autoclaving is carried out subsequently this is a disadvantage because a residue of disinfectant continues to function effectively during autoclaving. And a residue of lubricant is obviously desirable to be effective later during operation of the moving parts of the turbine.

SUMMARY OF THE INVENTION

The present invention provides a method of simultaneously flushing, disinfecting and lubricating a dental handpiece having an air-driven turbine and an air exhaust into which during operation air is introduced under pressure through a releasably connected flexible hose which includes an air drive line and an exhaust line. Some dental debris may remain in such a handpiece after operation. The first step of the method is to cease operation of the handpiece and disconnect it from the flexible hose. Next the handpiece is connected to a fitting having a first fluid line communicating with the turbine and a second fluid line communicating with the exhaust. A single liquid solution comprising a disinfectant and a lubricant is then pressurized. The pressurized solution is introduced through the first fluid line to the turbine to flush any debris therefrom so as to exit through the second fluid line from the exhaust and directly out of the handpiece. At the conclusion of these steps a residuum of solution is left in the turbine handpiece.

A preferred form of the method includes introducing compressed air into the first fluid line to admix with the pressurized liquid solution to assist in flushing debris from the turbine. A preferred disinfectant is chlorhexidine gluconate and a preferred lubricant is one other than petroleum based, specifically an alcohol such as glycerin. The method may include the step of filtering the debris from the solution exiting from the exhaust.

A chip air line may be included in the handpiece and hose for mixing pressurized air and a liquid in a spray during operation of the handpiece and a coolant line may be included as well. The method then includes the step of also introducing the pressurized single solution into the chip air line and/or the coolant line to flush debris directly out of the handpiece. A housing may be placed over the handpiece during flushing to contain the solution and debris exiting directly from the handpiece. The second fluid line carrying fluid from the handpiece exhaust may direct that fluid back into the housing. The housing may be transparent and heat-resistant and may include a pan for collecting solution and debris flushed from the handpiece.

The method may also include the step of sterilizing the turbine handpiece under heat and pressure in an autoclave after the residuum of solution is left therein and this may be done on the detached handpiece alone or with the housing remaining in place over the handpiece.

DESCRIPTION OF PREFERRED EMBODIMENT

Figure 1:
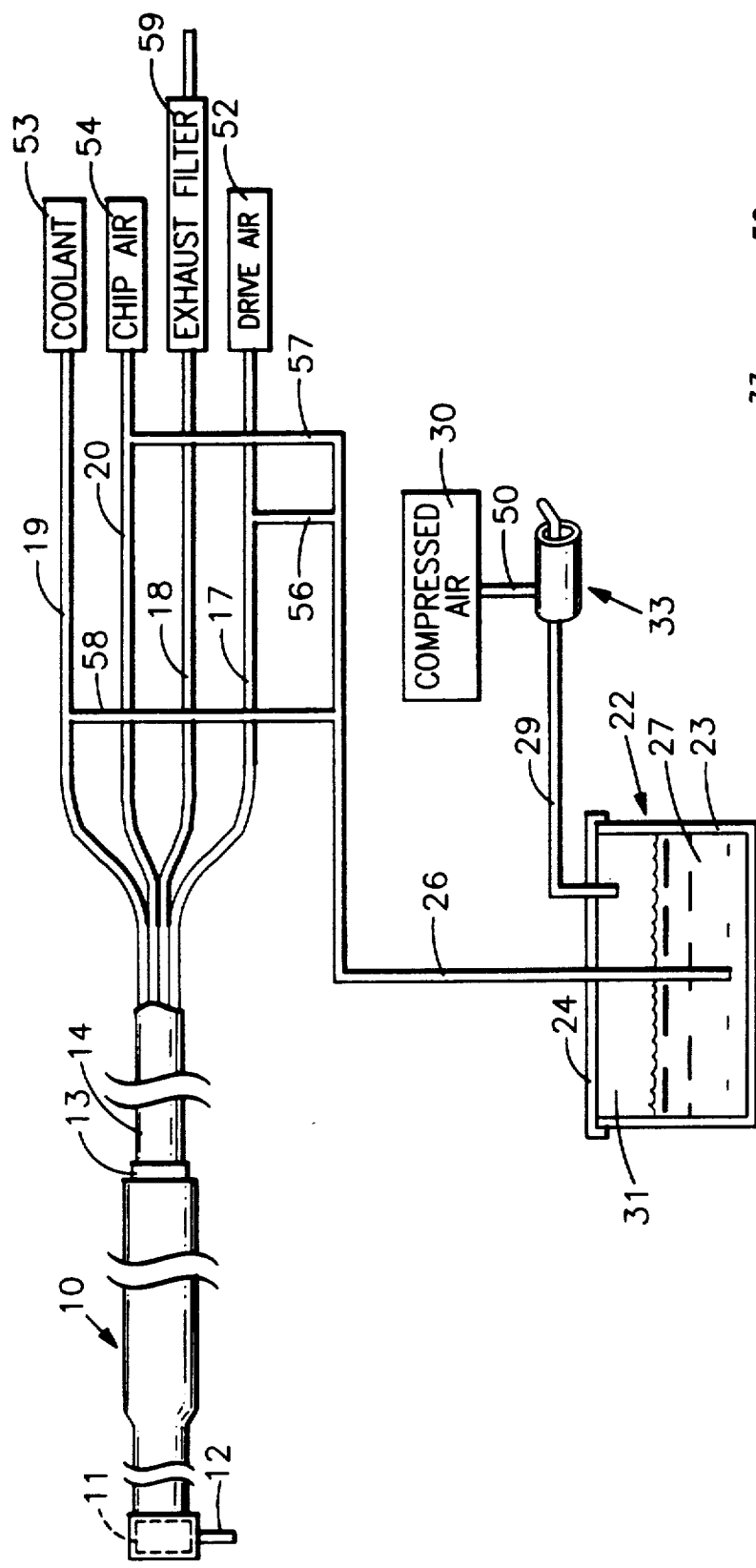
FIG. 1 is a schematic illustration partly broken away of the overall system for practicing one form of the method of the invention.

Referring first to the embodiment of FIG. 1 a dental turbine handpiece 10 includes a turbine 11 at its operating end for driving a selected dental tool 12. The handpiece 10 is removably attached by an end fitting 13 to a composite flexible hose 14 which extends to a conventional dental block.

The composite hose 14 of a typical high-speed turbine handpiece 10 includes four separate lines. One is a drive air line 17 though which compressed air is supplied to the turbine 11 to drive the turbine. That drive air is returned through the composite hose 14 in an exhaust line 18 and exits within the dental unit to the atmosphere. High-speed turbine handpieces also commonly include a coolant line 19 which proves a liquid coolant directly to the work site in the patient's mouth. Compressed air may be carried through the composite hose 14 through what is known as a chip air line 20, the purpose of which is to mix pressurized air with the coolant to provide a spray which can be directed to the work site in the patient's mouth.

Apparatus is known for providing a liquid additive solution to dental oral water-injection systems as described in my U.S. Pat. No. 4,668,190 and certain components of that apparatus are useful in carrying out the method of the present invention. Thus a reservoir 22 may be included which includes a cylindrical open-topped canister 23. The canister 23 has a screw-type lid 24 provided with a central hole through which a solution delivery line 26 extends downwardly close to the bottom of the canister 23. The canister 23 may be unscrewed from its lid 24 and partially filled with the preferred nonpetroleum based liquid disinfectant-lubricant solution 27 such as a mixture of chlorhexidine gluconate, water and an alcohol such as glycerin. The percentage of chlorhexidine gluconate in the solution may range from about 0.12% to 10.0% by weight. The percentage of glycerin in the solution should not exceed 50% by weight lest it cause clogging of the turbine.

Figure 2:
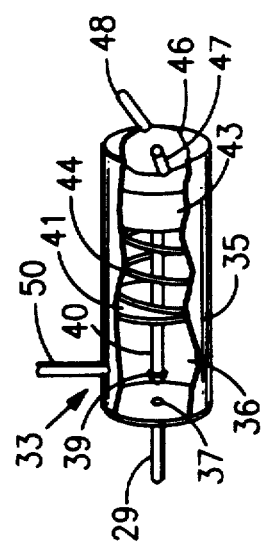
FIG. 2 is an enlarged pictorial view partly broken away of a valve for delivering the lubricant and disinfectant solution under pressure on demand.

A pneumatic pressure line 29 extends through the lid 24 from a compressed air source 30 into an ullage chamber 31 within the reservoir 22 over the solution 27. As shown in FIG. 2 manually operable pneumatic means 33 is provided for selectively introducing compressed air into the ullage chamber 31. The means include a cylindrical housing 35 which defines a chamber 36. Through a hole 37 the end of the pneumatic pressure line 29 communicates with the chamber 36. A needle valve 39 mounted on a stem 40, which passes through a stop element 41, is arranged to open and close the hole 37. At the opposite end of the stem 40 it is connected to a plunger 43 slidable in air-sealed relation with the interior of the housing 35. A compression spring 44 is biased between the plunger 43 and the stop element 41.

At the extreme end of the housing 35 is a cam 46 pivoted about an axle 47 and having a manual actuator arm 48. The cam 46 is configured such that when it is turned by the arm 48 about the axle 47 it urges the plunger 43 to the left as shown in FIG. 2 to compress the spring 44 and close the needle valve 39 to seat within and seal the hole 37 opening into the pressure line 29. By turning the arm 48 in an opposite direction the plunger 43 is moved to the right as shown in FIG. 2 by the force of the compression spring 44 to withdraw the needle valve 39 from the hole 37 causing the pressure line 29 to be in communication with the chamber 36. Through a line 50 the chamber 36 is in communication with the compressed air source 30. By these means compressed air may be introduced from the compressed air source 30 through the pressure line 29 by selective operation of the actuator arm 48.

The method of the embodiment of FIGS. 1 and 2 of the invention will now be described. As noted previously the method has as its purpose the flushing, disinfecting and lubricating of the dental turbine handpiece 10 into which during operation air is introduced under pressure through the drive line 17 from a drive air source 52 which after driving the turbine exits through the exhaust line 18. During operation of the handpiece 10 coolant is introduced from a coolant source 53 through the line 19 and, as noted previously, it may be mixed into a spray with compressed air from a chip air source 54 which is carried to the handpiece through the line 20.

The first step of this form of the method is to cease the operation of the handpiece 10, typically upon completion of dental work on a given patient. At this point the drive air source 52, the coolant source 53 and the chip air source 54 are all closed off from their respective lines leading to the handpiece 10, though the exhaust line 18 remains open to the atmosphere. The pneumatic means 33 is then operated to open the compressed air source 30 to the ullage chamber 31 in the reservoir 22. This forces the disinfectant-lubricant solution 27 upwardly through a supply tube 26. The supply tube 26 branches so that some of the pressurized disinfectant-lubricant solution passes through a sub-line 56 into the drive air line 17 and some of the solution passes through a sub-line 57 into the chip air line 20 and through a sub-line 58 into the coolant line 19. The turbine 11 of the handpiece 10 is disinfected by the solution entering it through the drive air line 17 and this solution flow dislodges and removes all of the dental debris which remains in the turbine 11. The flow of solution with the dental debris exits both back out the exhaust line 18 and also directly from the head of the handpiece 10. A filter 59 is provided adjacent the exit end of the exhaust line to collect all of the dental debris carried by the solution for proper disposal. The disinfectant-lubricant solution passing through the handpiece 10 through the chip air line 20 and the coolant line 19 exits directly from the operating end of the handpiece adjacent the tool 12 thus insuring that the parts of the handpiece 10 downstream from the turbine 11 are properly disinfected. The actuator arm 48 of the pneumatic means 33 is then operated to close off the compressed air source 30 from the ullage chamber 31 of the reservoir 22 thus ceasing introduction of the pressurized solution into the drive line 17 and the chip air line 20. However, a residuum of the solution is left throughout the handpiece 10 and its turbine 11.

The handpiece 10 is then disconnected by means of the end fitting 13 from the flexible hose 14 and the lines which it contains. The common practice is then to sterilize the handpiece 10 in an autoclave under heat and pressure. Thereafter the handpiece 1 is reconnected by the end fitting 13 to the flexible hose 14 and the drive air line 17, the exhaust line 18, the coolant line 19 and the chip air line 20 therewithin.

Compressed air from the drive air source 52 and the chip air source 54 is then introduced through the drive air line 17 and the chip air line 20 respectively to blow out most of the residuum of solution from the turbine handpiece. In doing so the glycerin component of the solution is left filming the moving parts of the turbine 11 to provide needed lubrication during subsequent operation. Some of that lubricant film subsequently is left within a patient's mouth and it is therefore preferable that it be a non-petroleum based substance which is the case with glycerin.

The second embodiment of the method of the invention will now be described with reference to FIG. 3. A dental turbine handpiece 70 including a turbine 71 is removably attachable by an end fitting 72 to a composite flexible hose similar to the hose 14 described in relation to FIG. 1. The handpiece 70 includes within its structure an air exhaust for returning driving air from the turbine 71, a coolant line and a chip air line for mixing pressurized air and a liquid coolant in a spray during operation of the handpiece. All of those components are similar to these systems for drive air, exhaust, chip air and coolant described in relation to the embodiment of FIG. 1.

Figure 3:
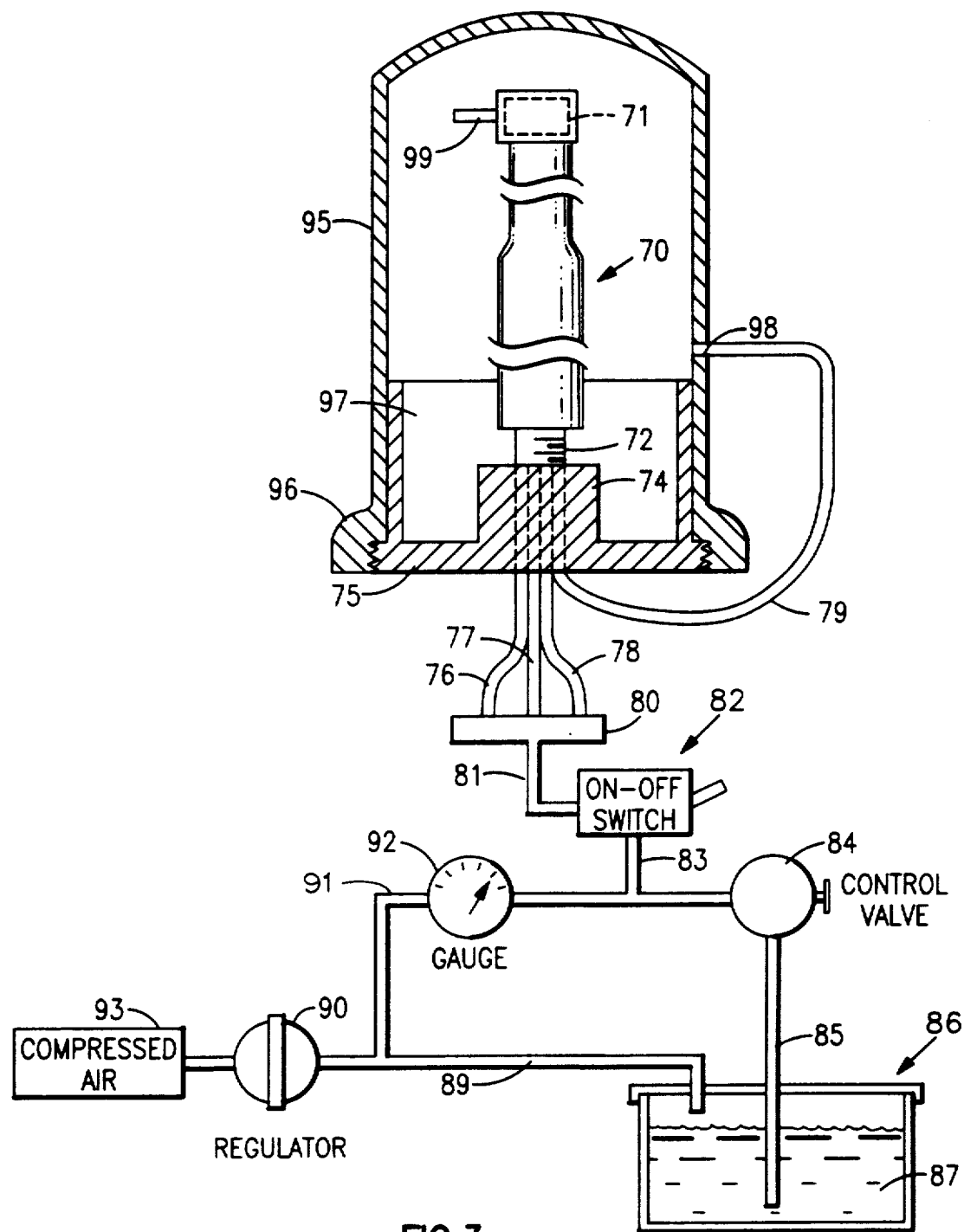
FIG. 3 is a schematic illustration partly broken away of another overall system for practicing another form of the method of the invention.

The first step in the method in the FIG. 3 embodiment is to cease operation of the handpiece 70 and disconnect it from its flexible hose. Its end fitting 72 is then screwed into a socket 74 which is part of a fitting 75 having a first fluid line 76 communicating with the turbine 71, a second fluid line 77 communicating with the coolant line, a third fluid line 78 communicating with the chip air line and a fourth fluid line 79 communicating with the exhaust. These four lines 76, 77, 78 and 79 come together in a union 80 supplied by a common line 81 equipped with an on/off switch 82 similar to the pneumatic control means 33 in FIGS. 1 and 2. An input line 83 of the switch 82 leads to a T-juncture, one leg of which is equipped with a control valve 84 leading to a solution delivery line 85. A reservoir 86 similar to the reservoir 22 described in relation to FIG. 1 is provided for holding a supply of the disinfecting and lubricating solution 87. Also as described in relation to FIG. 1 a pneumatic pressure line 89 extends into the reservoir 86. Compressed air is carried through the pressure line 89 from the output side of a pressure regulator 90 which also delivers compressed air through a line 91 equipped with a pressure gauge 92 leading to the T-junction at the input line 83. A source of compressed air 93 supplies the input side of the pressure regulator 90.

After the handpiece 70 is screwed into the socket 74 on the fitting 75 a transparent housing 95 is placed on the fitting 75 to enclose the handpiece 70 as shown in FIG. 3. This may be accomplished by a threaded circular periphery of the fitting 75 receiving an internally threaded circular base 96 on the housing 95. A cylindrical flange may extend upwardly about the outer upper edge of the fitting 75 to provide a pan 97 within the housing. The exhaust line 79 may be brought around from the fitting 75 to connect with the interior of the housing 95 through an appropriate hole 98.

As noted above the method as practiced on the system of FIG. 3 commences with the connection of the handpiece 70 to the socket 74 of the fitting 75 as shown. With the on/off switch 82 in closed position, compressed air from the solution 93 pressurizes the single liquid solution in the reservoir 86 comprising a chlorhexidine gluconate disinfectant and an alcohol lubricant such as glycerin. The control valve 84 is set to an appropriately selected flow adjustment position which may be increased or decreased as desired. The switch 82 is then turned to open position and a mixture of compressed air from the line 91 and pressurized liquid from the line 85 passes through the lines 83 and 81. In the union 80 this air-liquid mixture proceeds through the first fluid line 76 communicating with the turbine 71 and because of the air admixed with the solution the turbine 71 is able to rotate. It is desirable to have a plain burr 99 on the power outlet of the turbine 71 rather than an actual tool for the safety of those working with the system. This mixture of air and solution flushes all dental debris from the turbine and passes back through the exhaust line 79 to enter the housing 95 and be contained within the pan 97. The mixture of compressed air and solution also passes through the coolant line 78 and the chip air line 79 to flush any dental debris in those lines out of the operating end of the turbine 71 adjacent the burr 99 and directly into the interior of the housing 95, again to be collected in the pan 97. By this sequence of steps a residuum of solution is left in all parts of the handpiece 70.

The housing 95 is then unscrewed from the fitting 75 and the handpiece 70 is unscrewed from the socket 74. A standard sterilization of the handpiece 70 in an autoclave may then follow.

Sterilization under heat and pressure in the autoclave may also be carried out by leaving the handpiece 70 screwed in place in the socket 74 and leaving the housing 95 in place on the fitting 75. The entire assembly of the housing 95 and fitting 75 enclosing the handpiece 70 may be placed in the autoclave. For this purpose a suitable disconnect is provided between the fluid lines 76, 77 and 78 and the union 80. By leaving the handpiece and the disinfectant-lubricant in the housing substantially improved sterilization can be achieved during the autoclaving process.

It is important in the practice of the method embodied in the system of FIG. 3 that a single fluid is involved in a single injection step, specifically a mixture of compressed air with a liquid of chlorhexidine gluconate disinfectant and an alcohol lubricant such as glycerin. This is in contrast to other methods where lubricating with one liquid is followed by disinfecting with another liquid.

The scope of the invention is to be taken from the following claims rather than from the preceding description of preferred embodiment.

I claim:

1. A method of simultaneously flushing, disinfecting and lubricating a dental handpiece having an air-driven turbine and an air exhaust into which during operation air is introduced under pressure through a releasably connected flexible hose which includes an air drive line and an exhaust line and in which handpiece some dental debris may remain after operation, which comprises
   a) ceasing operation of the handpiece and disconnecting it from the flexible hose,
   b) connecting the handpiece to a fitting having a first fluid line communicating with the turbine and a second fluid line communicating with the exhaust,
   c) pressurizing a single liquid solution comprising a disinfectant and a lubricant,
   d) introducing the pressurized solution through the first fluid line to the turbine to flush any debris therefrom so as to exit through the second fluid line from the exhaust and directly out of the handpiece, and
   e) leaving a residuum of the solution in the handpiece.

2. A method according to claim 1 which includes the step of introducing compressed air into the first fluid line to admix with the pressurized liquid solution to assist in flushing debris from the turbine.

3. A method according to claim 1 wherein the disinfectant is chlorhexidine gluconate.

4. A method according to claim 1 wherein the lubricant is other than petroleum based.

5. A method according to claim 4 wherein the lubricant is an alcohol.

6. A method according to claim 5 wherein the alcohol is glycerin.

7. A method according to claim 1 which includes the step of filtering the debris from the solution exiting from the exhaust.

8. A method according to claim 1 wherein a chip air line is included in the handpiece and hose for mixing pressurized air and a liquid coolant in a spray during operation of the handpiece, and in which method the step is included of also introducing the pressurized solution into the chip air line to flush debris directly out of the handpiece.

9. A method according to claim 1 wherein a coolant line is included in the handpiece and hose, and in which method the step is included of also introducing the pressurized solution into the coolant line to flush debris directly out of the handpiece.

10. A method according to claim 1 which includes the step of placing a housing over the handpiece during flushing to contain the solution and debris exiting directly from the handpiece.

11. A method according to claim 10 wherein the second fluid line carrying fluid from the handpiece exhaust directs that fluid back into the housing.

12. A method according to claim 10 wherein the housing is transparent and heat-resistant.

13. A method according to claim 10 wherein the housing includes a pan for collecting solution and debris flushed from the handpiece.

14. A method of simultaneously flushing, disinfecting and lubricating a dental handpiece having an air driven turbine and an air exhaust into which during operation air is introduced under pressure through a releasably connected flexible hose which includes an air drive line and an exhaust line, the handpiece and hose also including a chip air line for mixing pressurized air and a liquid coolant in a spray during operation of the handpiece and a coolant line, in which handpiece some dental debris may remain after operation, which comprises
   a) ceasing operation of the handpiece and disconnecting it from the flexible hose;
   b) connecting the handpiece to a fitting having four fluid lines communicating respectively with the turbine, the coolant line, the chip air line and the exhaust;
   c) pressurizing a single liquid solution comprising a chlorhexidine gluconate disinfectant and an alcohol-based glycerin lubricant;
   d) introducing the pressurized solution and simultaneously introducing compressed air into the fluid lines to flush any debris from the handpiece so as to exit from the exhaust and directly from the handpiece;
   e) placing a transparent heat-resistant housing over the handpiece during flushing to contain the solution and debris exiting directly from the handpiece and collecting the same in a pan within the housing; and
   f) leaving a residuum of the solution in the handpiece.

15. A method according to claim 14 which includes the step of sterilizing the turbine handpiece under heat and pressure after the residuum of solution is left therein.

16. A method according to claim 14 wherein the housing is left in place over the handpiece during the sterilizing step.

* * * * *